US012133989B2

(12) United States Patent
Buchanan et al.

(10) Patent No.: US 12,133,989 B2
(45) Date of Patent: Nov. 5, 2024

(54) MEDICAL DEVICE HOUSING

(71) Applicant: Physio-Control, Inc., Redmond, WA (US)

(72) Inventors: Cathlene Buchanan, Shoreline, WA (US); Chris Egbert, Redmond, WA (US); Barry D. Curtin, Seattle, WA (US); David Wesche, Woodinville, WA (US); Ken Dickenson, Bellevue, WA (US)

(73) Assignee: Physio-Control, Inc., Redmond, WA (US)

( * ) Notice: Subject to any disclaimer, the term of this patent is extended or adjusted under 35 U.S.C. 154(b) by 787 days.

(21) Appl. No.: 17/162,695

(22) Filed: Jan. 29, 2021

(65) Prior Publication Data

US 2021/0236831 A1  Aug. 5, 2021

Related U.S. Application Data

(60) Provisional application No. 62/922,243, filed on Jan. 31, 2020.

(51) Int. Cl.
*A61N 1/39*  (2006.01)

(52) U.S. Cl.
CPC .................................. *A61N 1/3904* (2017.08)

(58) Field of Classification Search
CPC .......................... A61N 1/3904; A61N 1/3968
See application file for complete search history.

(56) References Cited

U.S. PATENT DOCUMENTS

| 5,645,586 A | 7/1997 | Meltzer |
| 2017/0157415 A1* | 6/2017 | Horseman ............ A61N 1/3975 |
| 2020/0094044 A1* | 3/2020 | Andrews ................ A61B 90/98 |

\* cited by examiner

*Primary Examiner* — Joseph M Dietrich
(74) *Attorney, Agent, or Firm* — Lee & Hayes, P.C.

(57) ABSTRACT

A medical device housing having a reduced footprint is described. The medical device housing includes a flange coupled to a first portion of the housing and a second portion of the housing that is configured to be coupled to the flange to substantially enclose an electronic component(s) within an interior of the medical device housing. The first portion of the housing includes a support(s) that supports the flange within the first portion. In some examples, a trench is formed between an interior wall of the first portion of the housing and the flange. An adhesive is deposited within the trench to bond the flange to the first portion of the housing. The second portion of the housing is configured to decouple from the flange to allow access to the interior of the medical device housing, such as for maintenance or repairs.

20 Claims, 7 Drawing Sheets

MEDICAL DEVICE HOUSING

CROSS-REFERENCE TO RELATED APPLICATION

This application claims the benefit of U.S. Provisional Application No. 62/922,243, titled "Medical Device Housing" and filed on Jan. 31, 2020, which is incorporated by reference herein in its entirety.

BACKGROUND

Electronic medical devices are used for various purposes, such as monitoring, diagnosing, and treating patients. A housing of a medical device, such as a defibrillator, is often designed to be resilient and durable due to the various conditions the medical device is expected to encounter during its use. The resilience and durability of the housing protects the internal components of the medical device from damage, such as when the medical device bumps into objects during transport, or when the medical device is dropped on the ground.

The housing of a medical device is typically constructed of two or more pieces of molded plastic that are coupled together using screws or other fasteners. In order to accommodate the fasteners, openings for the fasteners are often defined in a relatively thick strip of material that bulges outward from the housing and extends around the entirety of the housing. This bulging portion of the housing does not house any electronic components of the medical device, yet increases the overall footprint of the medical device, negatively impacting the portability, storage, and other usability aspects of the device. In some instances, a bulging portion of the housing makes it difficult to position the medical device relative to a patient during an emergency in which the patient is being treated. This hinders the efficiency and effectiveness of treating the patient by making it more difficult for a user, such as an emergency responder, to use the medical device. Further, a bulging portion of the housing of the medical device makes it difficult to store the medical device in a storage space or compartment, such as during transport or when the device is not being used. The disclosure made herein is presented with respect to these and other considerations.

DETAILED DESCRIPTION

Figure 1A:
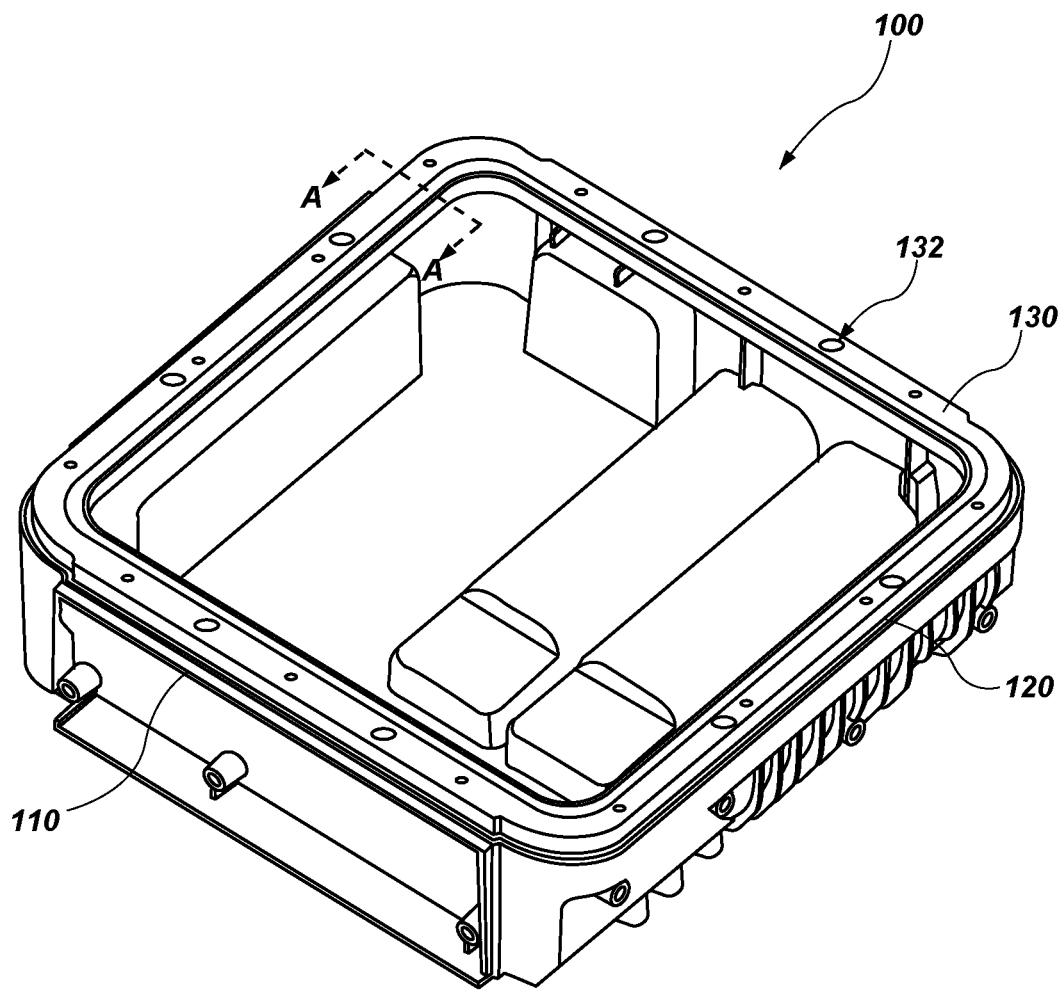
FIG. 1A illustrates an example partial housing of a medical device that includes a first portion of the housing and a flange coupled to the first portion of the housing.

A footprint of a medical device, such as a defibrillator, if too large or cumbersome, inhibits the ease of using the medical device by making it more difficult to transport, position, and store the medical device. A typical medical device has a housing that includes a bulging portion that protrudes outward to accommodate fasteners for joining two portions of the housing together. The conventional medical device housings that bulge outward in this fashion have a relatively large footprint; however, the bulging portion contains no components (e.g., electronic components) that are core to the function of the medical device. Instead, the bulging portion exists solely as a securing element to join portions of the medical device housing together.

The disclosure provides a medical device housing with a reduced footprint to facilitate transporting, positioning, and storing the medical device. Various implementations described herein relate to a medical device housing, a medical device that includes the housing, and processes involving the housing of the medical device, such as processes for forming (e.g., assembling) the housing of the medical device. The medical device housing described herein includes a flange that is configured to couple two portions of the medical device housing together without the need for excess material, such as the bulging material that exists on conventional medical device housings, as described above. This, in turn, produces a medical device housing having a reduced, or relatively small, footprint. By reducing the footprint of the medical device, less storage space is consumed in order to store the medical device, such as within a bag or a tote used to transport the medical device, or within a vehicle or a building. By consuming less storage space, the remainder of the available storage space allocable to other items, such as other equipment besides the medical device, is increased. This produces a medical device that is more portable and easier to store and use, as compared to conventional medical devices with relatively large and cumbersome housings. Additionally, the reduced footprint of the medical device allows the medical device to be more easily transported to, and positioned next to, a patient receiving treatment. The increased ease of use of the medical device increases the efficiency and effectiveness of using the medical device, such as to treat and monitor a patient.

The housing of a medical device disclosed herein is configured to contain various internal components of the medical device, such as various electronic components. According to some examples, the components of the medical device are configured to be mounted or secured within the housing, and are configured to provide functionalities and features of the medical device during operation of the medical device. According to some examples, the medical device housing includes a first portion (sometimes referred to herein as a "rear portion", a "rear housing portion", or a "first housing portion") having a closed end, an open end, and an interior wall between the closed end and the open end. The medical device housing further includes a second portion (sometimes referred to herein as a "front portion", a "front housing portion", or a "second housing portion").

According to some examples, the first and second portions of the housing are configured to be coupled together to form the housing of the medical device. A flange is configured to couple the two portions of the housing together and to provide an anchor for one or both of the portions of the housing. In an example, the flange is coupled to the first portion of the housing by at least one of snap-fitting the flange into the first portion of the housing, an adhesive that couples the flange to the first portion of the housing, by a fastener(s) that couples the flange to the first portion of the housing, or a combination thereof. The second portion of the housing is configured to be coupled to the flange in order to couple the two portions of the housing together.

According to some examples, the flange is configured to be coupled (e.g., bonded) to the first portion of the housing about the interior wall of the first portion of the housing, and the second portion of the housing is configured to be coupled to the flange to create an interior of the medical device housing and to substantially enclose one or more electronic components of the medical device within the interior of the housing. An electronic component(s) of the medical device is considered to be "substantially enclosed" if, after coupling the second portion of the housing to the flange, the housing prevents user access to the electronic component(s) without decoupling the second portion of the housing from the flange. According to some examples, the housing includes one or more openings into the interior and is still considered to substantially enclose the internal component(s) of the medical device if a user is unable to access the internal component(s) without decoupling the second portion of the housing from the flange. According to some examples, an exterior surface of the second portion of the housing is substantially aligned with an exterior surface of the first portion of the housing when the second portion of the housing is coupled to the flange. The alignment of the exterior surfaces of both portions of the housing eliminates the bulging portion of a typical housing of a medical device.

According to some examples, the flange is configured to be coupled to the first portion of the housing and positioned at least partially within the interior of the first portion of the housing so that the flange extends along the interior wall of the first portion of the housing and is positioned at or near an open end of the first portion of the housing. The open end of the first portion of the housing is the end of the first portion of the housing that couples to the second portion of the housing. According to some examples, the flange is shaped to fit at least partially within the first portion of the housing, such as by nesting the flange within the first portion of the housing about the interior wall of the first portion of the housing. According to some examples, one or more supports extend from the interior wall of the first portion of the housing to support the flange when the flange is positioned (e.g., nested) within the first portion of the housing.

Figure 5:
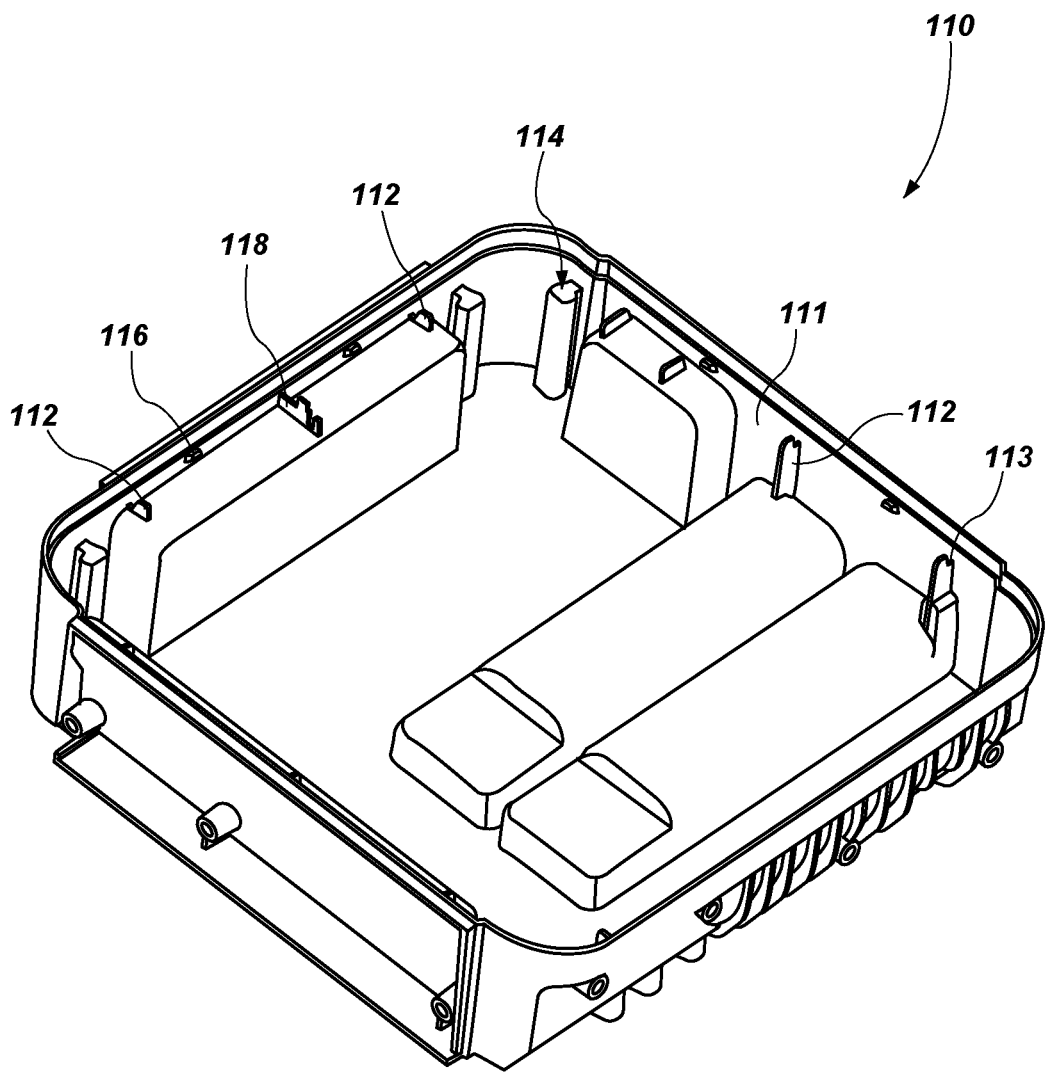
FIG. 5 illustrates the example first portion of the housing depicted in FIG. 1A without a flange coupled thereto.

Turning now to FIG. 1A, an example partial housing 100 of a medical device is shown that includes a first portion 110. FIG. 1A shows the first portion 110 of the housing with a flange 130 coupled (e.g., bonded) to the first portion 110. A cavity is defined in the first portion 110 of the housing to create an interior of a medical device, such as a defibrillator, in which the various components of the medical device are to be contained. According to some examples, the components (e.g., electronic components) to be contained in the interior of the medical device are mounted to the first portion 110 of the housing. FIG. 5 depicts the interior wall 111 (sometimes referred to herein as an "interior side wall") of the first portion 110 of the housing. The interior wall 111 extends about a periphery of the cavity defined in the first portion 110 of the housing. The first portion 110 of the housing has a closed end on one side of the interior wall 111 and an open end on the other side of the interior wall 111. The first portion 110 of the housing shown in FIG. 1A is in the shape of a rectangular cuboid with five rectangular faces. In this example, the cavity defined in the first portion 110 of the housing is cuboidal, and the interior wall 111 includes four planar sections and four rounded corners. It is to be appreciated, however, that the first portion 110 of the housing can be implemented in other suitable shapes, such as other types of polyhedrons, such as a square cuboid with an open end, a cylinder with an open end, or any other suitable shape, and the faces of the polyhedron may be any suitable polygonal shape.

According to some examples, the first portion 110 of the housing has various features defined in the interior surfaces of the first portion 110 and various features extending from the interior surfaces of the first portion 110. The interior surfaces of the first portion 110 include the surfaces of the interior wall 111, as well as the interior surface of the closed end of the first portion 110. In some examples, at least some of the features defined in, or extending from, the interior surfaces of the first portion 110 are configured to interface with the flange 130 for positioning and orienting the flange 130 within the first portion 110. According to some examples, the various features include pedestals, columns, surfaces, recesses, protrusions, or the like, onto or into which the flange 130 is configured to be nested.

The flange 130 shown in FIG. 1A is sized and shaped to extend along an entirety of interior wall 111 of the first portion 110 of the housing. In other examples, the flange 130 extends along some, but not all, of the interior wall 111. In an example where the first portion 110 of the housing is in the shape of a rectangular cuboid with five rectangular faces, the flange 130 has a rectangular (e.g., square) shape, as shown in FIG. 1A. According to some examples, the flange 130 includes a cutout in the center to produce a flange 130 in the form of a frame including four substantially straight strips of material joined by four rounded corners. According to some examples, the flange 130 is a multi-part element, and the individual parts of the flange 130 extend along a portion of the interior wall 111 of the first portion 110 of the housing 150. In an example, the flange 130 is a four-part element, and the individual parts of the flange 130 are coupled (e.g., bonded) to a portion of the interior wall 111 at a corner of the first portion 110 of the housing 150. In this example, the four parts of the flange 130 are curved to nest in the corners of the first portion 110. The use of a multi-part flange 130 reduces the overall weight of the medical device, as compared to using a monolithic flange 130, and the multi-part flange 130 also uses less material to produce or create the flange 130.

According to some examples, the flange 130 nests in the first portion 110 of the housing next to the interior wall 111 of the first portion 110, and the flange 130 is positioned at or near the open end of the first portion 110, near where the second portion 140 meets the first portion 110 when the second portion 140 is coupled to the flange 130. According to some examples, the flange 130 has an front surface 131 (See FIGS. 2-4) that is configured to contact the second portion 140 of the housing when the second portion 140 is coupled to the flange 130. According to some examples, an exterior surface 136 (See FIGS. 2-4) of the flange 130 extends orthogonally from the front surface 131 of the flange 130. The flange 130 shown in FIGS. 2-4 includes a lip 134 (sometimes referred to herein as a "flared portion") that flares away from the exterior surface 136. In some examples, the lip 134 extends along the entirety of the flange 130 at the rear end of the flange 130, which is the end closer to the closed end of the first portion 110. When the flange 130 is nested at least partially within the first portion 110, the exterior surface 136 of the flange 130 is substantially parallel to, and spaced apart from, the interior wall 111 of the first portion 110 of the housing. In this configuration, the lip 134 of the flange 130 contacts the interior wall 111 of the first portion 110 of the housing to space the exterior surface 136 of the flange 130 from the interior wall 111 of the first portion 110. The contact between the lip 134 of the flange 130 and the interior wall 111 of the first portion 110 forms a trench (sometimes referred to herein as a "channel", or a "trough") that is bounded by the exterior surface 136 of the flange 130, the lip 134 of the flange 130, and the interior wall 111 of the first portion 110. The lip 134 of the flange 130 is complimentary to the interior wall 111 of the first portion 110 of the housing by having a similar shape and size to that of the interior wall 111 so that the trench is continuous about the interior of the first portion 110 of the housing. When coupled to the first portion 110 of the housing, the flange 130 creates an interface (e.g., an anchor) that assists with coupling the second portion 140 of the housing to the first portion 110 of the housing, thereby forming the completed housing 150 of the medical device shown in FIG. 1B. According to some examples, the housing 150 represents a housing 150 of a defibrillator, such as an external defibrillator (e.g., an automated external defibrillator (AED)). As used herein, the term "couple" may refer to an indirect coupling or a direct coupling between elements. The term "couple," as used herein, may also refer to a removable coupling or a permanent coupling between the elements. Elements are removably coupled if a user or another entity is able to decouple the elements. Elements are permanently coupled if a user or another entity is unable to decouple the elements without destroying or significantly damaging the elements, or without undue effort to dissemble the elements using tools or machinery. As used herein, the term "couple" can be interpreted as connect, attach, join, engage, interface, link, fasten, or bind. Unless otherwise specified herein, the term "couple" is to be interpreted as coupling elements in a mechanical sense, rather than in an electrical sense, for example. Nevertheless, it is to be appreciated that a mechanical coupling of elements may result in an electrical coupling(s) between multiple elements of the system.

According to some examples, the second portion 140 of the housing 150 is configured to be removably coupled to the flange 130, such as by using one or more releasable fasteners, such as screws or other fastener(s) (e.g., pins, bolts, etc.). The releasable fastener(s) allow the second portion 140 of the housing 150 to be decoupled from the flange 130 after being coupled to the flange 130. By unfastening the releasable fasteners, the two portions 110, 140 of the housing 150 are configured to be decoupled to allow the two portions 110, 140 of the housing 150 to be separated and to permit access to the interior of the medical device housing 150. In an example, one or more screw(s) are used to couple the second portion 140 of the housing 150 to the flange 130. These screw(s) are configured to be unscrewed and removed to allow the second portion 140 of the housing 150 to be decoupled from the flange 130, allowing the first and second portions 110, 140 of the housing 150 to be separated and to permit access to the components (e.g., electronic components) of the medical device to perform maintenance or repairs.

The flange 130 includes openings 132 to facilitate coupling of the second portion 140 of the housing 150 to the first portion 110 of the housing 150 using the flange 130. In an example, the openings 132 are configured to receive fasteners, such as screws or other fastener(s) (e.g., pins, bolts, etc.), to couple the first and second portions 110 and 140 of the housing 150. According to some examples, the openings 132 are threaded or the openings 132 include, or are configured to receive, threaded inserts, and the threads allow screws or other threaded fasteners to be threaded into the openings 132 to couple the second portion 140 to the flange 130, which is coupled to the first portion 110. In another example, the openings 132 are through holes that allow fasteners to pass through the flange 130 to couple the second portion 140 to the flange 130, such as by using bolt and nut fasteners. In another example, the through hole openings 132 allow the first and second portions 110 and 140 of the housing to be coupled directly, such as by passing a fastener from the second portion 140, through the openings 132 in the flange 130, and coupling the fastener to the first portion 110. In another example, the second portion 140 includes physical features, such as locking tabs, that interface with the flange 130, such as by interfacing with slits or other types of openings in the flange 130 that are configured to receive and retain the locking tabs of the second portion 140, thereby coupling the second portion 140 to the flange 130. In yet another example, the second portion 140 includes protrusions that are configured to be received within the openings 132 in the flange 130. In some examples, the second portion 140 is coupled to the flange 130 by an adhesive that is placed within the openings 132 and that bonds to the protrusions extending from the second portion 140 of the housing 150. When the second portion 140 of the housing 150 is coupled to the flange 130, one or more components (e.g., electronic components) are substantially enclosed within the interior of the housing 150.

The housing 150, or portions thereof, may be made of any suitable material, combination of materials, or composite materials. According to some examples, the housing 150 of the medical device is made of a semi-rigid material or a rigid material, such as a polymer material including a thermoplastic polymer, such as acrylonitrile butadiene styrene (ABS) plastic, or a similar material. According to some examples, the housing 150, or portions thereof, are manufactured using an injection molding technique, or an extrusion technique, the processes for which should be apparent to a person having ordinary skill in the art. By using an injection molding method to manufacture the housing 150, or portions thereof, minimal material is used for the manufacture of the housing 150, thereby preventing excess waste of material. Other manufacturing techniques that may be used to manufacture the housing 150 include machining a material into the shape of the housing 150. According to some examples, another subtractive manufacturing technique are used besides machining. According to some examples, an additive manufacturing technique, such as 3D printing, is used to manufacture the housing 150, or portions thereof.

According to some examples, the flange 130 is configured to be positioned within the first portion 110 of the housing 150, and an adhesive 120 (sometimes referred to herein as a "bonding agent") is disposed between the flange 130 and the first portion 110 of the housing 150 to couple (e.g., bond) the flange 130 to the first portion 110. According to some examples, the adhesive 120 is used to permanently couple the flange 130 to the first portion 110 of the housing 150. The positioning (e.g., nesting) of the flange 130 within the first portion 110 forms a trench 122 (See FIG. 6B) between the exterior surface 136 of the flange 130 and the interior wall 111 of the first portion 110. In an example, the flange 130 and first portion 110 of the housing 150 are each shaped so that the trench 122 is formed between the flange 130 and the first portion 110 of the housing 150 when the flange 130 is nested at least partially within the first portion 110 of the housing 150. In this example, the trench 122 is formed between the exterior surface 136 of the flange 130 and the interior wall 111 of the first portion 110 of the housing 150, and the trench 122 extends along the interior wall 111. The adhesive 120 is deposited into the trench 122 between the flange 130 and the first portion 110 (See FIG. 2), and the adhesive 120 is allowed to cure in order to permanently couple the flange 130 to the first portion 110 of the housing 150. In some examples, the adhesive 120 is a viscous or gel-like material so that the adhesive 120 is expressed into, and settles in, the trench 122. In an example, the adhesive 120 is an acrylic adhesive. The ability of the adhesive 120 to flow and settle into the trench 122 increases the surface area of both the flange 130 and the interior wall 111 of the first portion 110 that is in contact with the adhesive 120, which forms a strong and sturdy coupling between the flange 130 and the first portion 110. The dispensed adhesive 120 cures in the trench 122 according to its associated bonding characteristics. Once cured, the adhesive 120 forms a seal between the flange 130 and the first portion 110. The bond between the flange 130 and the first portion 110 assists with limiting intrusion of environmental matter into the interior of the housing 150 of the medical device, such as moisture, fluids, and other contaminants. This provides a housing 150 that is waterproof, or otherwise "element"-proof. It also provides a housing 150 that is shockproof because the strength of the bond between the flange 130 and the first portion 110 of the housing 150 prevents decoupling of the flange 130 and the first portion 110 when the housing 150 is inadvertently dropped on the ground or bumped during transit, and the adhesive 120 absorbs shock due to the material properties of the adhesive 120.

In an example, a person deposits the adhesive 120 into the trench 122 that is formed between the flange 130 and the interior wall 111 of the first portion 110. In another example, an automated depositor deposits the adhesive 120 into the trench 122. In this example, the automatic depositor is configured to dispense and deposit the adhesive 120 throughout the trench 122 in a controlled manner according to preset instructions. In an example, an automated depositor is configured to deposit the adhesive 120 into the trench 122 in the controlled manner, such as by rate of deposition of the adhesive 120 or a rate of travel of the automated depositor. According to some examples, the automated depositor includes a dispensing apparatus (e.g., a needle) that is configured to dispense the adhesive 120 and deposit the adhesive 120 into the trench 122. In an example, the dispensing apparatus of the automated depositor is positioned within the trench 122 (e.g., by extending the dispensing apparatus from the automated depositor) to dispense the adhesive 120 while positioned within the trench 122. During the deposition process, the automated depositor moves about the flange 130 (which is nested at least partially within the first portion 110 of the housing 150) to deposit the adhesive 120 throughout the trench 122. According to some examples, the adhesive 120 is deposited into the trench 122 as a liquid (e.g., a gel), and the liquid either hardens into a solid or solidifies but remains pliable when cured, depending on the type of adhesive 120 used and the needs of the particular medical device. According to some examples, multiple passes or deposition processes are implemented to deposit a particular amount of adhesive 120 into the trench 122.

In another example, the adhesive 120 is configured to cure exothermically, and multiple passes of the automated depositor to deposit the adhesive 120 within the trench 122 are implemented to achieve desired properties of the bond between the flange 130 and the first portion 110 of the housing 150. According to some examples, the use of multiple passes to deposit the adhesive 120 allows different adhesives to be deposited within the trench to bond the flange 130 to the first portion 110 of the housing 150. In an example, the automated depositor is configured to deposit a first adhesive within the trench 122 during a first pass, and to deposit a second adhesive within the trench 122 during a second pass. In this example, the combination of multiple, different adhesives achieves a desired property(ies) or characteristic(s) of the bond between the flange 130 and the first portion 110 of the housing 150. According to some examples, in between sequential passes, a first adhesive deposited within the trench 122 is given time to at least partially cure prior to depositing a second adhesive within the trench 122 on a subsequent pass. According to some examples, various adhesives, environments, or a combination thereof are used to assist with curing the adhesive(s) 120, such as depositing a secondary material to the adhesive 120 or exposing the adhesive 120 to ultraviolet (UV) light.

According to some examples, the flange 130 and the first portion 110 of the housing 150 form an enclosed channel when the flange 130 is nested within the first portion 110. In an example, the flange 130 include a protrusion running along the exterior surface 136 and positioned a distance away from the lip 134 of the flange 130. When this example flange 130 is nested at least partially within the first portion 110, the lip 134 of the flange 130, the exterior surface 136 of the flange 130, the protrusion extending from the exterior surface 136 of the flange 130 a distance from the lip 134, and the interior wall 111 of the first portion 110 form the enclosed channel, with the lip 134 and the protrusion of the flange 130 contacting the interior wall 111 of the first portion 110 and extending along the entire interior wall 111 of the first portion 110. To permanently couple the flange 130 to the first portion 110, the adhesive 120 is deposited into the channel. In an example, a person or an automated depositor deposits the adhesive 120 between the lip 134 and the protrusion of the flange 130 along an entire periphery of the flange 130, and the flange 130 is nested in the first portion 110 to create the enclosed channel and to couple (e.g., bond) the flange 130 to the first portion 110.

Figure 1B:
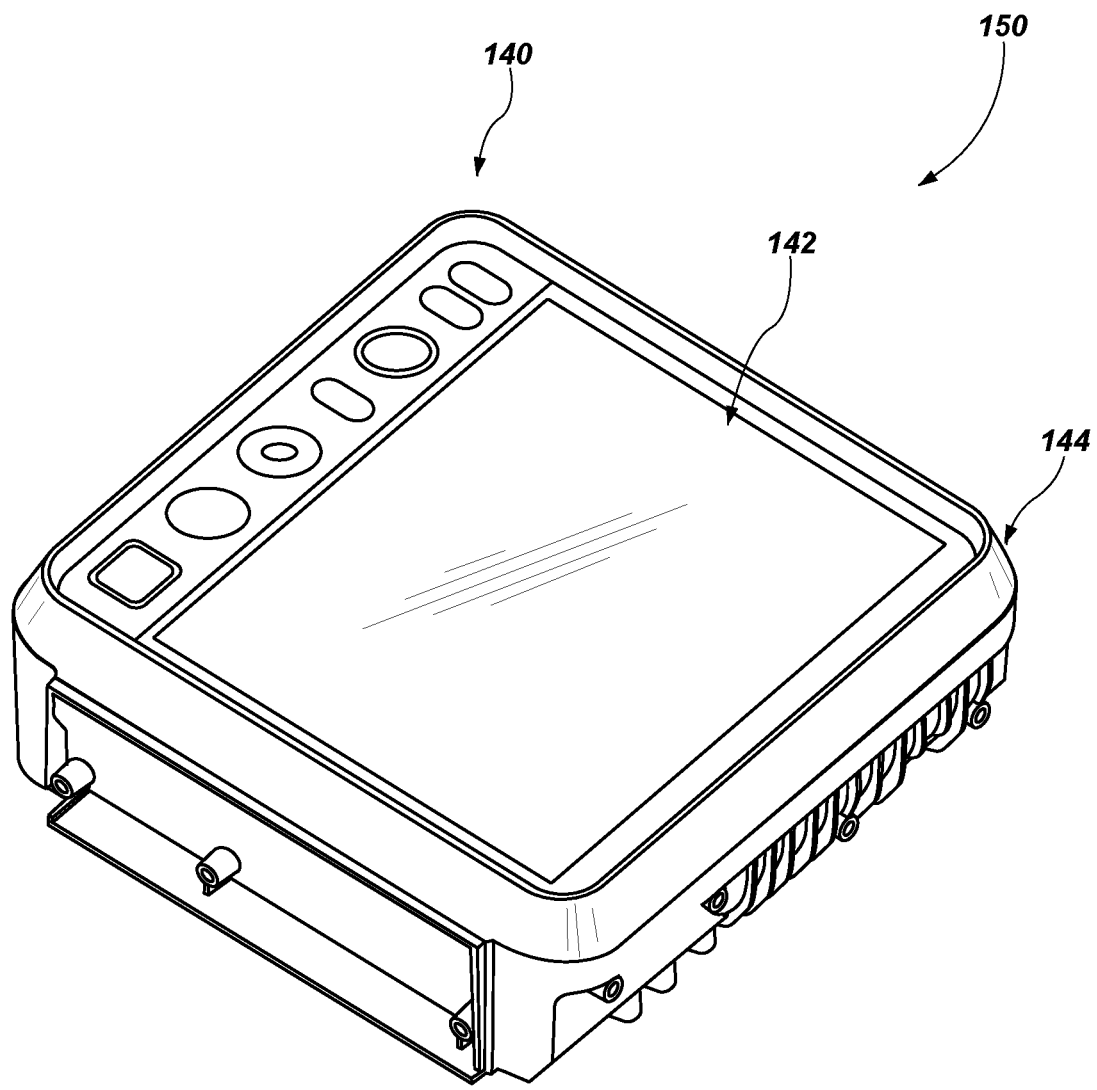
FIG. 1B illustrates an example second portion of a housing of a medical device, the second portion of the housing coupled to the first portion of the housing depicted in FIG. 1A.

FIG. 1B illustrates the second portion 140 of the housing 150 coupled to the flange 130 to substantially enclose one or more components (e.g., electronic components) of the medical device within the interior of the housing 150. In an example, the second portion 140 of the housing 150 includes a body portion 142 and a bezel 144. According to some examples, the body portion 142 includes various components of the medical device, such as a user interface(s), an output(s), controls, other features relating to the operability of the medical device, or a combination thereof. According to some examples, the various components of the body portion 142 are interconnected, and the body portion 142 is configured to be coupled to the flange 130. According to some examples, the various components of the body portion 142 are individually and independently coupled to the flange 130. That is, in an example, the body portion 142 includes components that are individually and independently configured to be coupled to the flange 130 as respective subassemblies. According to some examples, the various components of the body portion 142 are electrically connected to other components of the medical device that are contained within the interior of the first portion 110. In an alternative example, the body portion 142 is a face of the medical device that includes one or more cut-outs or openings to allow access to various components, functions, or features of the medical device, such as those contained within the interior of the medical device. In the example of FIG. 1B, the body portion 142 is square-shaped and is sized to be complementary to the flange 130. According to some examples, the body portion 142 is configured to be coupled to the flange 130 using one or more fasteners (not shown), such as fasteners that are configured to be inserted into the openings 132 in the flange 130. According to some examples, the fasteners used to couple the body portion 142 to the flange 130 are removable to allow the body portion 142 to be decoupled from the flange 130, such as to allow a user access to the various components within the medical device for maintenance or repairs.

According to some examples, the bezel 144 extends around the body portion 142 along a periphery of the body portion 142 to cover the fasteners that are used to couple the body portion 142 to the flange 130. The bezel 144 also prevents, or reduces, intrusion of environmental matter (e.g., moisture) into the interior of the medical device. According to some examples, the bezel 144 is press fit onto the body portion 142 and is removable from the body portion 142 by a user pulling the bezel 144 off of the body portion 142 to provide the user with access to the fasteners that are used to couple the body portion 142 to the flange 130. After the bezel 144 is removed, a user or another entity is able to decouple the two portions 110, 140 of the housing 150 by unfastening the fasteners, which are made accessible by removal of the bezel 144. According to some examples, the second portion 140 of the housing 150 includes a gasket(s) that abuts the flange 130 when the second portion 140 is coupled to the flange 130, the gasket(s) being configured to prevent intrusion of environmental matter into the interior of the medical device housing when the second portion 140 is coupled to the flange 130. According to some examples, the gasket(s) is/are placed between the flange 130 and the first portion 110 of the housing 150, between the flange 130 and the second portion 140 of the housing 150, between the first and second portions 110, 140 of the housing 150, or between other elements of the housing 150.

Figure 2:
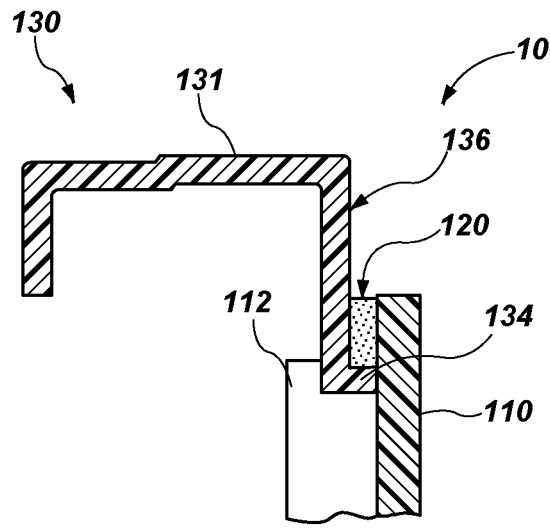
FIG. 2 illustrates a cross-section view of respective portions of the flange and the first portion of the housing depicted in FIG. 1A, as well as an adhesive that bonds the flange to the first portion of the housing, and a support that supports the flange.

FIG. 2 illustrates an example cross-section view of a portion of the flange 130, the adhesive 120, and the first portion 110 of the housing 150 of a medical device, taken along section line A-A shown in FIG. 1A. The flange 130 shown in FIG. 2 includes the lip 134 that extends from the rear end of the exterior surface 136 of the flange 130. When the flange 130 is nested within the interior of the first portion 110, the lip 134 contacts the interior wall 111 of the first portion 110 of the housing 150. The trench 122 is formed about the periphery of the flange 130 between the interior wall 111 of the first portion 110 of the housing 150 and the exterior surface 136 of the flange 130, with the lip 134 providing the base of the trench 122. In the example of FIG. 2, the adhesive 120 is deposited into the trench 122 to couple the flange 130 to the first portion 110 of the housing 150. According to some examples, one or more supports 112 (sometimes referred to herein as "flange supports"), such as columns, supports, or ledges, are configured to support the flange 130 when the flange 130 is positioned (e.g., nested) within the first portion 110 of the housing 150. In FIG. 2, the flange 130 is shown as resting on the support 112 which positions the flange 130 at a particular position (e.g., level) within the first housing portion 110. The support 112 extends from the interior wall 111 of the of the first portion 110 of the housing 150 and is shaped to receive and support the flange 130 when the flange 130 is positioned (e.g., nested) within the first portion 110. In an example, the support 112 is rectangular in shape with a cutout defined in a front end of the support 112 to receive the lip 134 of the flange 130 within the cutout. According to some examples, the support 112 is positioned on a ledge within the first portion 110. In other examples, the support 112 is positioned on any suitable interior surface of the first portion 110 of the housing 150, as shown in FIG. 5.

According to some examples, the lip 134 of the flange 130 has a profile(s) configured to maintain the adhesive 120 within the trench 122 prior to the adhesive 120 curing. In an example, the profile of the lip 134 of the flange 130 is shaped to maintain the uncured adhesive 120 within the trench 122. In some examples, the profile of the lip 134 of the flange 130 is shaped to provide increased surface area with which the adhesive 120 is in contact. As shown in FIG. 2, the adhesive 120 contacts the exterior surface 136 of the flange 130. Additionally, a viscosity of the adhesive 120 is such that the adhesive 120 is prevented from flowing out of the trench 122.

Figure 3:
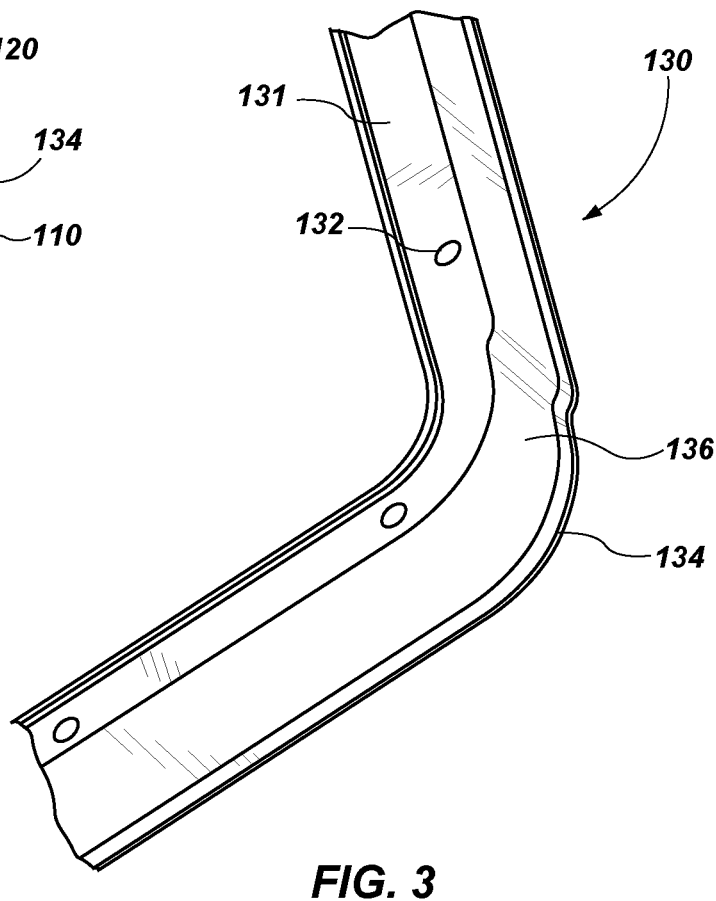
FIG. 3 illustrates a detailed view of a portion of the flange depicted in FIG. 1A.
Figure 4:
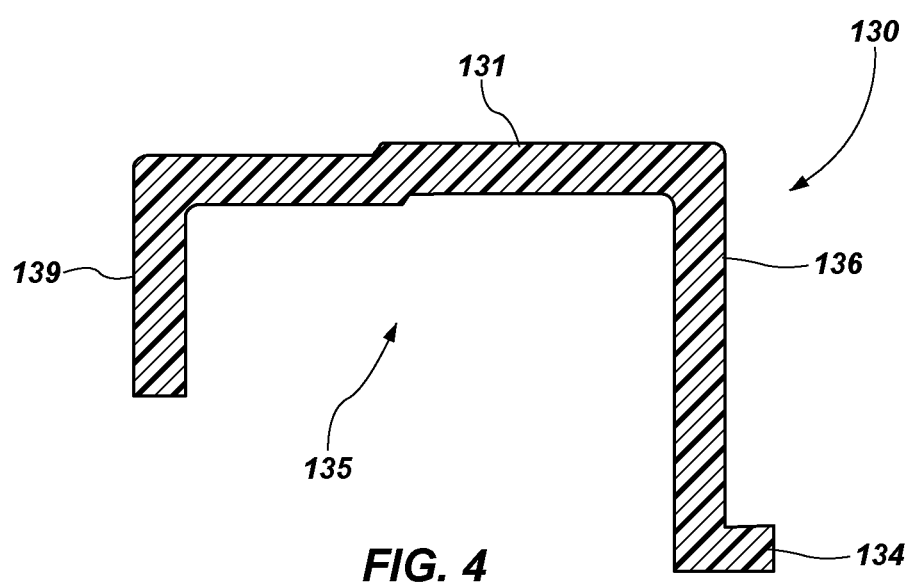
FIG. 4 illustrates a cross-section view of a portion the flange depicted in FIG. 1A.

FIG. 3 illustrates a detailed view of a portion (e.g., a corner portion) of the example flange 130 depicted in FIG. 1A. In FIG. 3, the portion of the flange 130 is shown as including the lip 134, the exterior surface 136, and the openings 132 defined in the front surface 131 of the flange 130. As shown in FIG. 3, the lip 134 protrudes from the exterior surface 136 at a rear end of the exterior surface 136 and runs along the periphery of the flange 130. According to some examples, a distance the lip 134 protrudes from the exterior surface 136 is substantially constant about the perimeter of the flange 130. The exterior surface 136 and the lip 134 of the flange 130 are shaped to allow the flange 130 to nest against the interior wall 110 of the first portion 110 of the housing 150, and upon nesting the flange 130 within the first portion 110, the trench 122 (See FIG. 6B) is formed between the flange 130 and the interior wall 111 of the first portion 110. The width of the trench 122 is based on the distance the lip 134 protrudes from the exterior surface 136, and, in some examples, the width of the trench 122 is substantially constant about the periphery of the flange 130 due to the substantially constant distance the lip 134 protrudes from the exterior surface 136 of the flange 130. According to some examples, the lip 134 protrudes from the exterior surface 136 at varying distances about the periphery of the flange 130, such as to provide additional surface area to which the adhesive 120 adheres, or to accommodate surface features on the interior wall 111 of the first portion 110. In an example, an interior surface 139 of the flange 130 is shaped differently than the exterior surface 136 of the flange 130. According to some examples, the interior surface 139 of the flange 130 is substantially square-shaped, while the exterior surface 136 and the lip 134 of the flange 130 are shaped to conform with the interior wall 111 of the first portion 110. In the example of FIG. 4, the interior surface 139 is shorter than the exterior surface 136.

FIG. 4 illustrates a cross-section view (e.g., the cross-section view of FIG. 2) of a portion of the example flange 130 depicted in FIG. 1A, but without showing the first portion 110, the support 112, and the adhesive 120. As described herein, the first portion 110 of the housing 150 includes one or more features, such a columns, ledges, or supports, that are configured to interface with the flange 130 to assist with positioning the flange 130 within the interior of the first portion 110 of the housing 150, and for supporting the flange 130. The supports 112 extending from the interior wall 111 of the first portion 110 are configured to engage the rear side 135, or at least portions of the rear side 135, of the flange 130 to support and position the flange 130 within the first portion 110. As shown in FIG. 2, the support 112 is in contact with a rear side 135 of the lip 134 of the flange 130 to support the flange 130 within the first portion 110 of the housing 150.

FIG. 5 illustrates an example first portion 110 of the housing 150 of a medical device. In contrast with FIG. 1A, however, a flange 130 is not coupled to the first portion 110 in FIG. 5 to illustrate the features of the first portion 110 occluded by the flange 130 in FIG. 1A. The first portion 110 depicted in FIG. 5 includes various features to assist with supporting and positioning the flange 130 within the first portion 110. In an example, one type of feature includes supports 112. The supports 112 have cutouts 113 (sometimes referred to herein as "notches") defined therein, the cutouts 113 being configured to interface with the flange 130 and position the flange 130, and the supports 112 configured to support the flange 130 within the first portion 110 of the housing. In FIG. 5, the cutouts 113 defined in the supports 112 are shaped to receive the lip 134 of the flange 130, which allows the flange 130 to be supported by the supports 112. In an example, the cutouts 113 defined in the supports 112 are square-shaped. According to some examples, multiple supports 112 are positioned about the interior wall 111 of the first portion 110 near (e.g., within a threshold distance from) the open end of the first portion 110 to stably support the flange 130. According to some examples, the supports 112 extend upward from a rear interior surface at the closed end of the first portion 110, and the supports 112. Additionally, or alternatively, the supports 112 extend from the interior wall 111 of the first portion 110 and extend along the interior wall 111. According to some examples, there is a space between a rear end of the supports 112 and the rear interior surface at the closed end of the first portion 110. In an example, the spacing of the supports 112 along the interior wall 111 of the first portion 110 is regular (e.g., the supports 112 are spaced at regular intervals along the interior wall 112) such that the adjacent supports 112 are equally spaced from one another. In another example, the spacing of the supports 112 about the interior wall 111 is irregular such that the spacing between adjacent supports 112 varies along the interior wall 111. In an example, the positions and the dimensions of the supports 112 are based on the packaging of the components that are to be contained in the interior of the medical device within the first portion 110 of the housing 150, such as to make the installation of the components easier and more efficient. According to some examples, other features of the interior of the first portion 110 coincide with the positions of the supports 112, and, in such situations, the supports 112 extend from those other features. In an example, the supports 112 extend upwards from respective features (e.g., projections, compartments, etc.) of the interior of the first portion 110.

According to some examples, the flange 130 is supported, at least in part, by pedestals 114. The flange 130, when nested in the first portion 110, is configured to rest upon the pedestals 114. In some examples, the pedestals 114 have planar front surfaces onto which a portion of the flange 130, such as the lip 134, and/or the rear side 135 of the flange 130, is configured to rest to support the flange 130 within the first portion 110. According to some examples, the front surfaces of the pedestals 114 include features that assist with positioning the flange 130 within the first portion 110 of the housing 150, such as notches, pins, or other positioning features. Similar to the supports 112, the pedestals 114, in some examples, extend upward from a rear interior surface at the closed end of the first portion 110. Additionally, or alternatively, the pedestals 114 extend from the interior wall 111 of the first portion 110 and extend along the interior wall 111. According to some examples, the pedestals 114 are positioned about the interior wall 111 of the first portion 110 such that the pedestals 114 are spaced at regular or irregular intervals. In the example shown in FIG. 5, the pedestals 114 are positioned at or near the corners of the first portion 110 of the housing 150. The positioning of support features with planar front surfaces, such as the pedestals 114, in the corners of the first portion 110 makes it easier to nest the flange 130 within the first portion 110, since the flange 130 does not have to be manipulated about positioning feature, such as notches, pins, or the like.

In FIG. 5, tabs 116 (sometimes referred to herein as "protrusions") are positioned about the interior wall 111 of the first portion 110 of the housing 150. In some examples, the tabs 116 are configured to engage the flange 130 to couple the flange 130 to (e.g., retain the flange 130 within) the first portion 110 when the flange 130 is nested in the first portion 110. The tabs 116 extend from the interior wall 111 and are positioned on the interior wall 111 at positions that allow the tabs 116 to engage the lip 134 of the flange 130 when the flange 130 is nested within the first portion 110. When the flange 130 is nested within the first portion 110, the supports 112 and the pedestals 114 provide support for the flange 130 by contacting the lip 134 of the flange 130 (e.g., from a rear side of the lip 134), and the tabs 116 retain the flange 130 in the first portion 110 by preventing the lip 134 from moving away from the supports 112 and the pedestals 114 (e.g., by the tabs 116 contacting a front side of the lip 134). In this manner, forwards and backwards motion (i.e., motion along an axis running from the closed end to the open end of the first portion 110 of the housing 150) of the flange 130 within the first portion 110 is prevented by the tabs 116, the supports 112, and the pedestals 114. According to some examples, the tabs 116 are distributed regularly or irregularly about the interior wall 111 and are positioned relative to, or independent from, the positions of the supports 112 and the pedestals 114. In the example of FIG. 5, multiple tabs 116 are shown, and an individual tab 116 is positioned between a pair of adjacent supports 112, such as by positioning the tabs 116 and the supports 112 along the interior wall 111 in an alternating manner.

According to some examples, the tabs 116 are positioned on the interior wall 111 a distance away from the cutouts 113 of the supports 112, and the tabs 116 are positioned closer to the open end of first portion 110 than the supports 112 by a distance that is substantially equal to a thickness of the lip 134 of the flange 130. In this manner, when the flange 130 is nested within the first portion 110 of the housing 150, the lip 134 moves behind the tabs 116 and the lip 134 is supported from behind by the supports 112 and the pedestals 114, and the lip 134 is restrained from the front by the tabs 116. Since the tabs 116 extend from the interior wall 111 and the lip 134 of the flange 130 is shaped and sized to contact the interior wall 111, the lip 134 of the flange 130 is configured to maneuver past tabs 116 and to rest upon the supports 112 and the pedestals 114 while the flange 130 is being nested in the first portion 110. In an example, pressure is exerted on the front surface 131 of the flange 130 to cause a portion of the flange 130, such as the lip 134, to flex or bend to allow the lip 134 to move past the tabs 116 and to be seated between the supports 112 and the pedestals 114 at the rear and the tabs 116 at the front. According to some examples, the tabs 116 are shaped to facilitate moving the lip 134 of the flange 130 past the tabs 116. In an example, a front surface of the tabs 116 is sloped in a direction from the front, open end of the first portion 110 towards the rear, closed end of the first portion 110, which causes the flange 130 to flex when the flange 130 is being nested in the first portion 110, thereby allowing the lip 134 to move past the tabs 116. Once the lip 134 of the flange 130 moves past the tabs 116, the flange 130 returns to its original shape due to the resilient nature of the flange 130 so that the lip 134 is positioned behind, and retained by, the tabs 116. This is an example of snap-fitting the flange 130 within the first portion 110 of the housing 150, and it represents one example way of coupling the flange 130 to the first portion 110. According to some examples, the tabs 116 are positioned about a portion of the interior wall 111, such as along one planar section of the interior wall 111, and the lip 134 of the flange 130 is configured to be inserted between the tabs 116 and the supports 112 along that portion of the interior wall 111 initially, and then the rest of the flange 130 is nested into the interior of the first portion 110 of the housing 150 by setting or pressing the rest of the flange 130 upon the supports 112 and pedestals 114 positioned along a remainder of the interior wall 111. The tabs 116 at least partially retain the flange 130 within the first portion 110 of the housing 150 by preventing movement of the flange 130 forwards and away from the supports 112 and the pedestals 114.

Figure 6A:
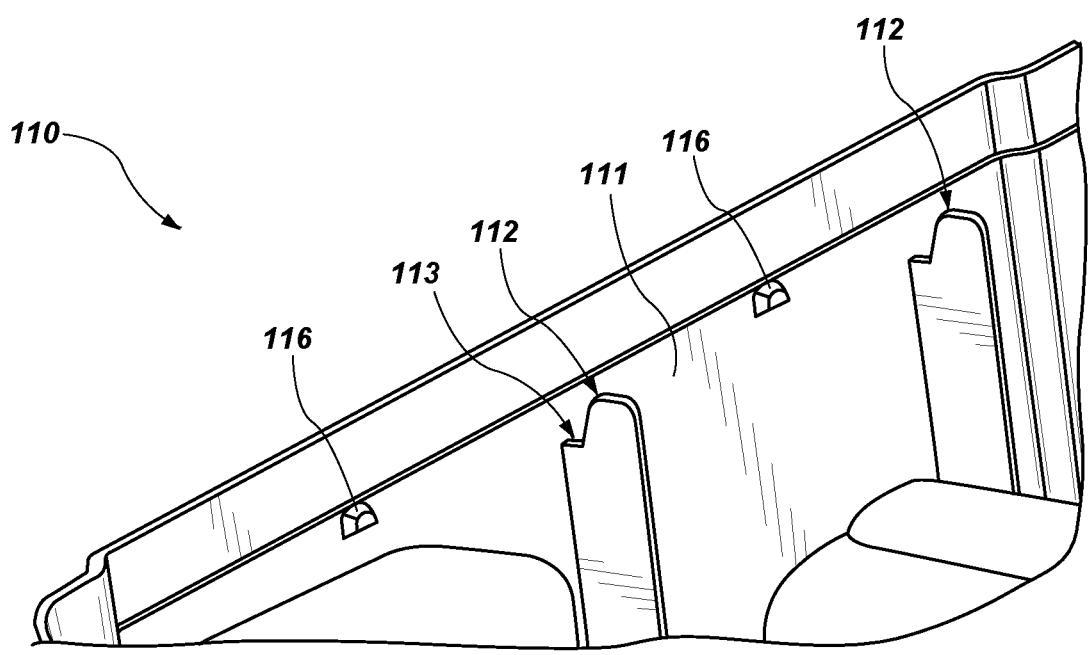
FIG. 6A illustrates a perspective view of an interior portion of the first portion of the housing of the medical device depicted in FIG. 5.

FIG. 6A illustrates a perspective view of an interior portion of the first portion 110 of the housing 150 of a medical device depicted in FIG. 5. Two supports 112 and two tabs 116 are shown in FIG. 6A. In the example shown, one of the tabs 116 is positioned between the two supports 112. In some examples, the tabs 116 are evenly spaced along the interior wall 111, and the supports 112 are also evenly spaced along the interior wall 111. In other examples, the tabs 116 or the supports 112, or both, are irregularly spaced along the interior wall 111, and the pattern of tabs 116 and supports 112 is repeating, such as by alternating between a tab 116 and a support 112 along the interior wall 111, or the pattern of the tabs 116 is non-repeating.

Figure 6B:
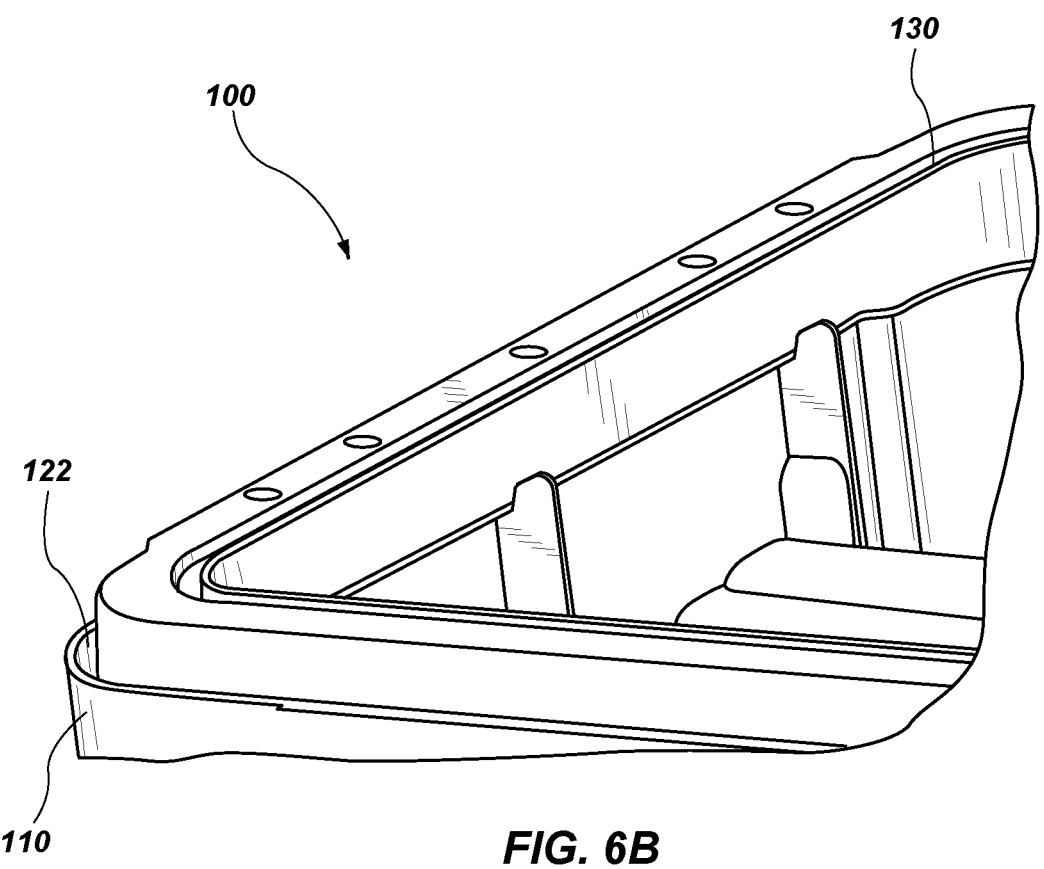
FIG. 6B illustrates a perspective view of the interior portion of the first portion of the housing of the medical device depicted in FIG. 6A with a flange coupled to the first portion of the housing of the medical device.

FIG. 6B illustrates a perspective view of the interior portion of the first portion 110 of the housing 150 of the medical device depicted in FIG. 6A with a flange 130 coupled to the first portion 110 of the housing of the medical device. According to some examples, the flange 130 is coupled to the first portion 110 of the housing 150 such that the lip 134 (not shown in FIG. 6B) of the flange 130 is retained from the front by the tabs 116 and supported from behind by the supports 112. As shown in FIG. 6B, the flange 130 is positioned to rest within the cutouts 113 of the supports 112. The lip 134 of the flange 130 abuts the interior wall 111 of the first portion 110 of the housing 150 to form the trench 122 into which the adhesive 120 is deposited.

Figure 7A:
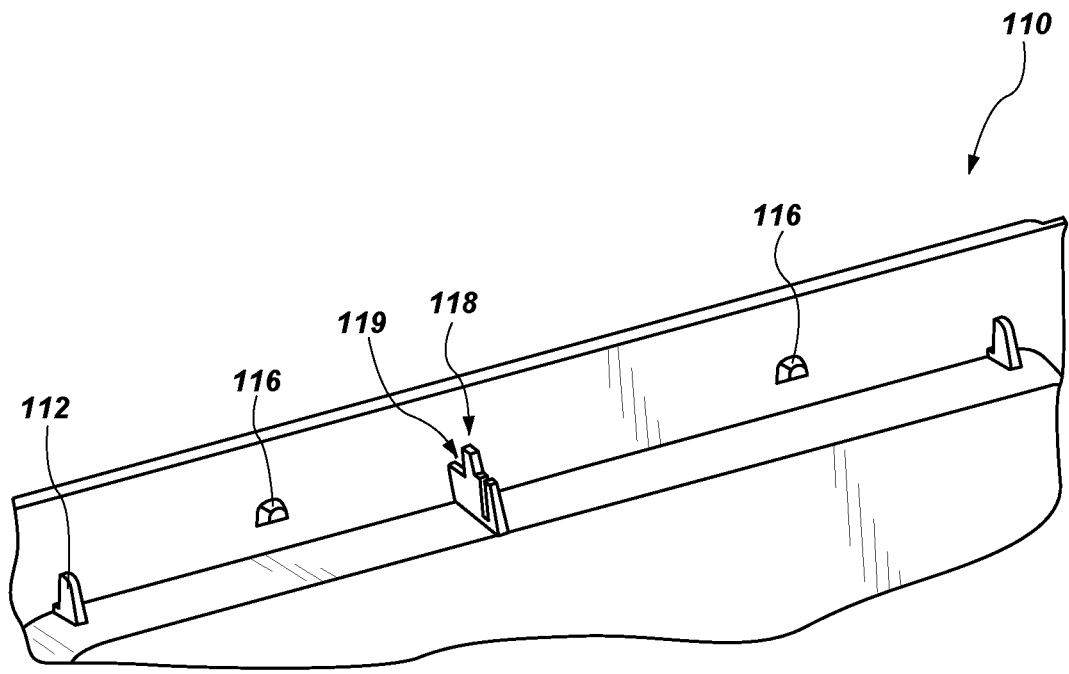
FIG. 7A illustrates a perspective view of another interior portion of the first portion of the housing of the medical device depicted in FIG. 5.

FIG. 7A illustrates a perspective view of another interior portion of the first portion 110 of the housing 150 of the medical device depicted in FIG. 5, such as different section of the interior wall 111 of the first portion 110 than that which is shown in FIGS. 6A and 6B. The portion of the interior of the first portion 110 shown in FIG. 7A includes a keying feature 118 that assists with properly orienting the flange 130 within the first portion 110. The keying feature 118 is positioned at a particular location along the interior wall 111 of the first portion 110 of the housing 150 and extends from the interior wall 111. The keying feature 118 is configured to engage a corresponding keying feature of the flange 130, such as a keying slot 138 (See FIG. 7B). The use of a keying feature 118 prevents the flange 130 from being nested within the first portion 110 in the wrong orientation. That is, the keying feature 118 is configured to prevent the flange 130 from fully nesting within the first portion 110 of the housing 150 if the flange 130 is not oriented correctly. In the example shown, the keying feature 118 includes a keying notch 119. The keying notch 119 is positioned closer to the open end of the first portion 110 than the cutouts 113 of the supports 112 are positioned to the open end. In this manner, when the flange 130 is placed within the first portion 110 of the housing 150, the lip 134 of the flange 130 is prevented from resting on the supports 112 and the pedestals 114 about the entire periphery of the flange 130 by the keying feature 118 and the keying notch 119, if the flange 130 is in the wrong orientation. That is, the lip 134 of the flange 130 is configured to catch on the keying notch 119 and the flange 130 will be oriented askew (i.e., not parallel to the closed end of the first portion 110) within the first portion 110 if the flange 130 is improperly oriented. According to some examples, alternative or additional keying features 118 that are configured to engage with the flange 130 are positioned on the interior wall 111 and are configured to assist with properly orienting the flange 130 within the first portion 110 of the housing 150.

Figure 7B:
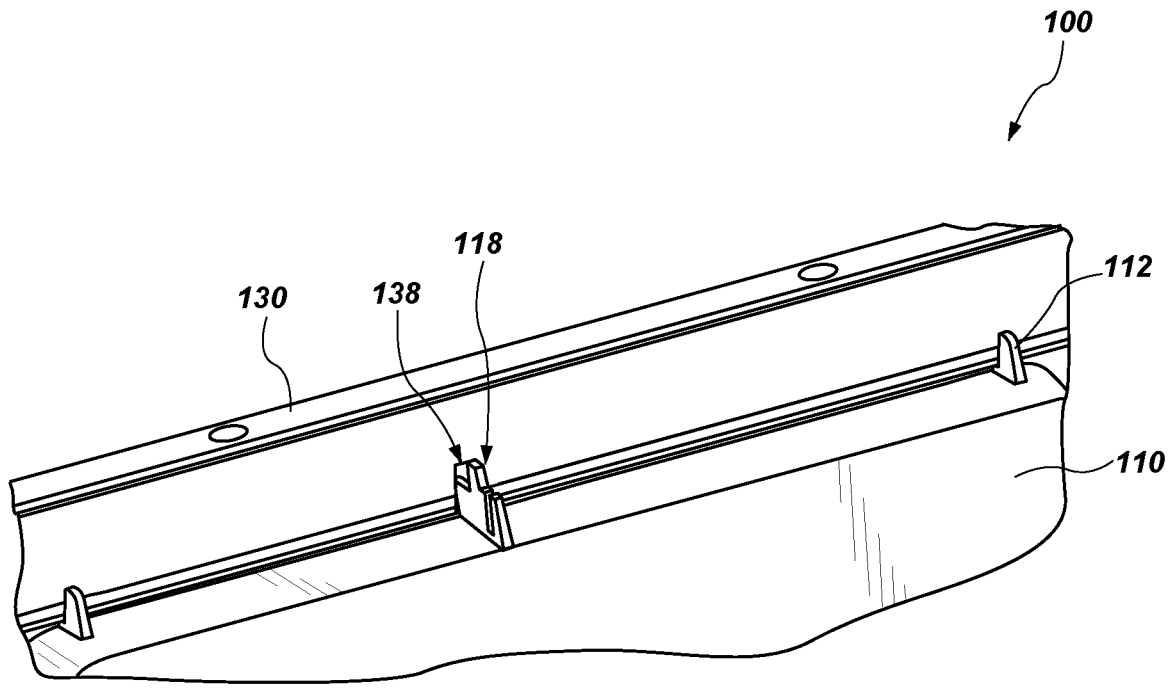
FIG. 7B illustrates a perspective view of the interior portion of the first portion of the housing of the medical device depicted in FIG. 7A with a flange coupled to the first portion of the housing of the medical device.

FIG. 7B illustrates the interior portion of the first portion 110 of the housing 150 depicted in FIG. 7A having a portion of the flange 130 nested within the first portion 110. The flange 130 includes the keying slot 138 defined in a rear side, and/or in the lip 134, of the flange 130, the keying slot 138 being configured to receive the keying feature 118 of the first housing portion 110. In an example, the keying slot 138 is positioned at a particular location along the lip 134 of the flange 130. The particular position of the keying feature 118 on the interior wall 111 of the first portion 110 and the particular position of the keying slot 138 on the flange 130 means that the flange 130 fully nestable within the first portion 110 exclusively when the keying feature 118 and the keying slot 138 are aligned with each other, which properly orients the flange 130 within the first portion 110 of the housing 150. According to some examples, the keying slot 138 is defined in the exterior surface 136 of the flange 130 and has a width sized to fit about the keying feature 118, which allows the lip 134 to be fully seated between the tabs 116 at the front and the supports 112 and pedestals 114 at the rear, as described herein. When the flange 130 is properly oriented and nested within the first portion 110, as depicted in FIG. 7B, the keying feature 118 is disposed within the keying slot 138.

The closeness of the fit of the keying slot 138 about the keying feature 118 is configured to prevent the adhesive 120 from flowing out of the trench 122 through the keying slot 138 and around the keying feature 118 while the adhesive 120 is being deposited in the trench 122 and while the adhesive 120 is curing. In an example, the keying slot 138 is sized (in terms of its width and height) to substantially contact the keying feature 118 so that any gaps between the keying slot 138 and the keying feature 118 are reduced, if not eliminated, to prevent the adhesive 120 from flowing out of the trench 122. According to some examples, the adhesive 120 includes one or more properties, such as a viscosity, that prevents or inhibits its flow through the keying slot 138 when deposited in the trench 122. In another alternative, a sealant or sealing material is deposited at the interface between the keying feature 118 and the keying slot 138 (i.e., where the two components engage one another) to prevent the flow of the adhesive 120 from the trench 122. The engagement of the keying feature 118 by the keying slot 138 allows the flange 130 to be nested within the first portion 110 of the housing 150 so that the lip 134 of the flange 130 rests on the support features, such as the supports 112 and the pedestals 114. A misalignment of the keying feature 118 and the keying slot 138 prevents the nesting of the flange 130 within the first portion 110, and an alignment of the keying feature 118 and the keying slot 138 allows the nesting of the flange 130 within the first portion 110. In this manner, a user is able to discern if the flange 130 is improperly oriented within the first portion 110 by observing that the flange 130 is askew or not nested in a level orientation within the first portion 110.

Figure 8:
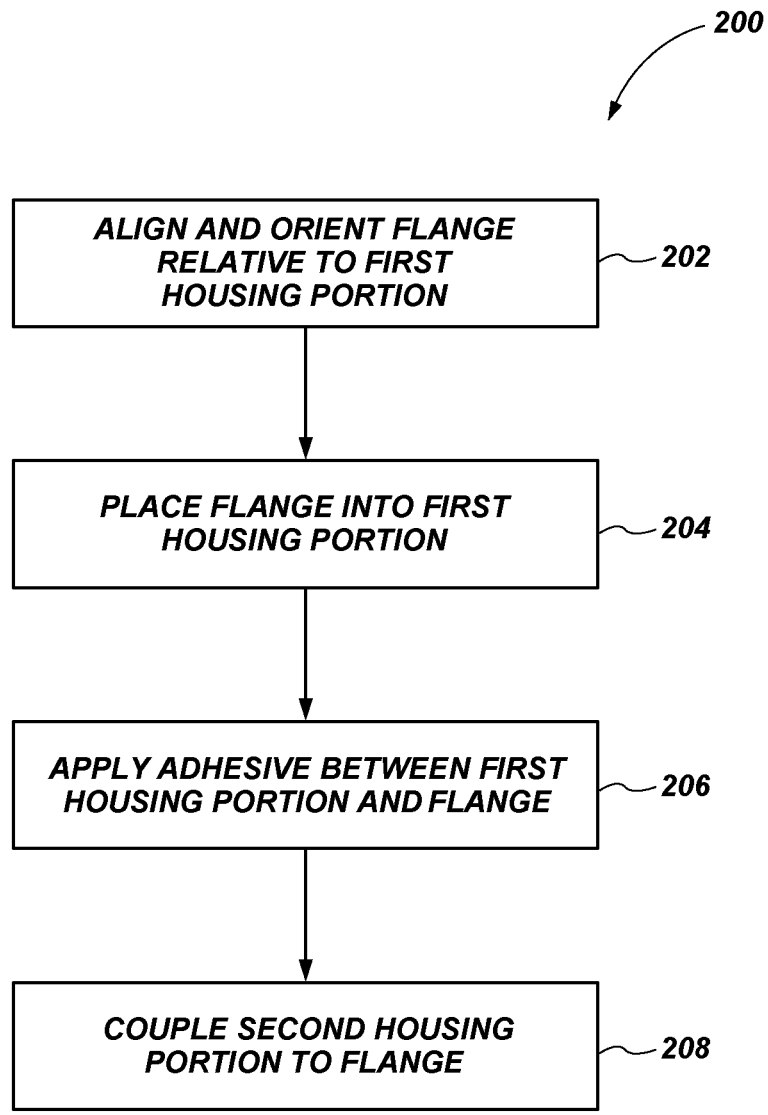
FIG. 8 illustrates an example process for forming a housing of a medical device.

FIG. 8 illustrates an example process related to various implementations of the present disclosure. Although FIG. 8 illustrates steps in a particular order, implementations are not limited to the specific order of operations illustrated in the figures. In various implementations, the process 800 is performed by an entity(ies) involved in manufacturing or assembling a medical device. According to some examples, the entity(ies) that perform the process 800 include a human, a robot or other autonomous machinery configured to assemble parts of a medical device, an automated depositor, or any combination thereof.

FIG. 8 illustrates an example process 200 for forming (e.g., assembling) a housing 150 of a medical device. At 202, a flange 130 is aligned and oriented relative to a first portion 110 of a housing 150 of a medical device. According to some examples, the flange 130 and the first portion 110 include features to help properly orient the flange 130 at block 202. In an example, the first portion 110 of the housing 150 includes a keying feature 118 and the flange 130 includes keying slot 138, and these keying features assist with properly orienting the flange 130 relative to the first portion 110 of the housing 150. In an example, block 202 involves aligning a keying feature 118 of the first portion 110 of the housing 150 with a keying slot 138 defined in the flange 130 to orient the flange 130 within the first portion 110 of the housing 150. According to some examples, the first portion 110 of the housing 150 includes supports 112 and other features (e.g., pedestals 114) that assist with positioning and supporting the flange 130 within the first portion 110 of the housing 150.

At 204, the flange 130 is placed (e.g., nested) at least partially within the first portion 110 of the housing 150. "At least partially", as used in this context, means that part of the flange 130 may stick out from, or protrude from, the open end of the first portion 110, as shown in FIG. 6B, for example. In other words, the flange 130 is considered to be nested in the first portion 110 despite a portion of the flange 130 (e.g., the front surface 131) being positioned in front of a most distal edge of the first portion 110 at the open end of the first portion 110. According to some examples, the first portion 110 of the housing 150 includes tabs 116 that extend from the interior wall 111 of the first portion 110 of the housing 150. The tabs 116 interface with the flange 130 at block 204 to retain the flange 130 within the first portion 110. In an example, the flange 130 is placed within the first portion 110 and pressed or otherwise manipulated to move the lip 134 of the flange 130 past the tabs 116 of the first portion 110 to seat the lip 134 between the tabs 116 at the front and the supports 112 and pedestals 114 at the rear, thereby nesting the flange 130 within the first portion 110 of the housing 150. In some examples, this represents a snap-fit type of coupling in order to couple the flange 130 to the first portion 110 of the housing 150.

At 206, an adhesive 120, in some examples, is applied at an interface between the first portion 110 of the housing 150 and the flange 130. In an example, a trench 122 is formed between the exterior surface 136 of the flange 130 and the interior wall 111 of the first portion 110 of the housing 150 after the flange 130 is nested within the first portion 110 (after block 204). In this example, the adhesive 120 is deposited into the trench 122 at block 206 to couple (e.g., bond) the flange 130 to the first portion 110 of the housing 150. According to some examples, the deposition of the adhesive 120 in the trench 122 is performed manually (e.g., by a user). In other examples, the deposition of the adhesive 120 in the trench 122 is performed automatically, such as by an automated depositor, as described herein. In an example, the adhesive 120 is a composite material, such as an epoxy, that is configured to bond components together. According to some examples, the depositing of the adhesive 120 includes depositing the adhesive 120 in multiple passes along the trench 122.

At 208, after the flange 130 is coupled to the first portion 110 (e.g., after the adhesive 120 is cured and the first portion 110 and the flange 130 are permanently coupled together), the second portion 140 of the housing 150 is coupled to the flange 130, such as by one or more releasable fasteners. In an example, the flange 130 includes openings 132 defined in a front surface 131 of the flange 130, and the openings 132 receive the fasteners at block 208 to couple the second portion 140 of the housing 150 to the flange 130, thereby coupling the second portion 140 to the first portion 110 to form the complete housing 150 of the medical device. According to some examples, at block 208, the second portion 140 of the housing 150 includes a bezel 144 that is press-fit about the periphery of a body portion 142 of the second portion 140 to cover the fasteners, and the bezel 144 is removable to allow access to the fasteners, such as for decoupling the second portion 140 of the housing 150 from the flange 130 to access internal components of the medical device.

EXAMPLE CLAUSES

1. A housing for a medical device, the housing including: a first portion including an interior wall and a support extending from the interior wall, the first portion of the housing configured to contain an electronic component of the medical device disposed therein; a flange coupled to the first portion of the housing, the flange nested at least partially within the first portion of the housing and supported by the support; and a second portion configured to be coupled to the flange to substantially enclose the electronic component within an interior of the housing when the second portion of the housing is coupled to the flange.
2. The housing of clause 1, wherein the flange and the interior wall form a trench that extends along the interior wall, the housing further including an adhesive disposed in the trench, the adhesive bonding the flange to the interior wall.
3. The housing of clause 2, wherein the flange includes a lip that extends from an exterior surface of the flange, and wherein the trench is formed by the exterior surface of the flange, the lip of the flange, and the interior wall.

4. The housing of clause 3, wherein the support is in contact with a rear side of the lip of the flange to support the flange within the first portion of the housing.

5. The housing of clause 3 or 4, wherein the first portion of the housing further includes a tab extending from the interior wall, and wherein the tab is in contact with a front side of the lip of the flange to retain the flange within the first portion of the housing.

6. The housing of any one of clauses 1 to 5, wherein the flange includes openings defined in a front surface of the flange, the openings configured to receive fasteners to couple the second portion of the housing to the flange.

7. The housing of any one of clause 6, wherein the second portion of the housing includes a bezel configured to cover the fasteners upon coupling the second portion of the housing to the flange.

8. The housing of any one of clauses 1 to 7, wherein the first portion of the housing includes a keying feature extending from the interior wall, wherein the flange includes a keying slot defined in a rear side of the flange, and wherein the keying feature is disposed within the keying slot to orient the flange within the first portion of the housing.

9. A medical device including: a housing to contain a component of the medical device, the housing including: a first portion including a closed end, an open end, and an interior wall between the closed end and the open end; a flange coupled to the first portion of the housing, the flange nested at least partially within the first portion of the housing and positioned at the open end; and a second portion configured to be coupled to the flange to substantially enclose the component within an interior of the housing when the second portion of the housing is coupled to the flange.

10. The medical device of clause 9, wherein the flange is in contact with the interior wall to form a trench between the flange and the first portion of the housing, and wherein the housing further includes an adhesive disposed within the trench, the adhesive bonding the flange to the first portion of the housing.

11. The medical device of clause 9 or 10, wherein the first portion of the housing further includes a support extending from the interior wall and supporting the flange within the first portion of the housing.

12. The medical device of any one of clause 11, wherein the flange includes a lip, and wherein a cutout is defined in the support to receive the lip of the flange.

13. The medical device of any one of clauses 9 to 12, wherein the first portion of the housing further includes a keying feature extending from the interior wall and disposed within a keying slot defined in the flange to orient the flange within the first portion of the housing.

14. The medical device of any one of clauses 9 to 13, wherein the flange includes a lip and an exterior surface from which the lip extends, and wherein the lip of the flange is in contact with the interior wall.

15. The medical device of any one of clauses 9 to 14, wherein the flange includes openings defined in a front surface of the flange, the openings configured to receive fasteners to couple the second portion of the housing to the flange.

16. A method of forming a housing of a medical device, the method including: nesting a flange at least partially within a first portion of the housing such that the flange comes into contact with a support extending from an interior wall of the first portion of the housing; and coupling a second portion of the housing to the flange.

17. The method of clause 16, wherein, after the nesting of the flange, a lip of the flange is in contact with the interior wall to form a trench between the flange and the first portion of the housing, the trench extending along the interior wall, and wherein the method further includes depositing an adhesive in the trench, the adhesive configured to bond the flange to the first portion of the housing when the adhesive is cured.

18. The method of clause 17, wherein the depositing includes depositing the adhesive using an automated depositor.

19. The method of any one of clause 17 or 18, wherein the depositing includes depositing the adhesive in multiple passes along the trench.

20. The method of any one of clauses 16 to 19, further including, prior to the nesting, aligning a keying feature of the first portion of the housing with a keying slot defined in the flange to orient the flange within the first portion of the housing.

21. A housing for a medical device, including: a first housing portion having an exterior perimeter, an interior wall, and a flange support positioned along the interior wall; a flange nested within the first housing portion and positioned to rest on the flange support, the flange and the interior wall of the first housing portion forming a trough that extends around the interior perimeter; a bonding agent applied in the trough to bond the flange to the first housing portion; and a second housing portion having an exterior perimeter shaped to mate with the exterior perimeter of the first housing portion and to attach to the flange.

22. The housing of clause 21, wherein the flange includes a lip that extends from an exterior vertical surface of the flange, and wherein the trough is formed by the lip of the flange, the exterior vertical surface of the flange and the interior wall of the first housing portion.

23. The housing of clause 22, wherein the flange support is configured to receive the lip of the flange.

24. The housing of clauses 22 or 23, wherein the interior wall of the first housing portion includes one or more tabs configured to contact the lip of the flange to retain the flange within the first housing portion.

25. The housing of any one of clauses 21 to 24, wherein the flange includes opening disposed on an upper surface of the flange, the openings configured to receive fasteners to attach the second housing portion to the flange.

26. The housing of clause 25, wherein the second housing portion includes a bezel configured to cover the fasteners that attach the second housing portion to the flange.

27. The housing of any one of clauses 21 to 26, wherein the first housing portion includes a keying feature and the flange includes a keying notch, the keying notch configured to fit about the keying feature to orient the flange within the first housing portion.

28. The housing of any one of clauses 21 to 26, wherein the bonding agent is at least one of acrylic adhesive.

29. A portable medical device, including: one or more components configured to provide at least one of a patient monitoring or a patient treatment capability of the medical device; and a housing configured to contain the one or more components, the housing including: a first housing portion having an interior wall; a flange nested within the first housing portion with at least a portion of the flange contacting the interior wall of the first housing portion to form a trough between the flange and the first housing portion; a bonding agent deposited within the trough to couple the flange to the first housing portion; and a second housing portion releasably coupled to the flange and configured to substantially enclose an interior of the housing.

30. The portable medical device of clause 29, wherein the first housing portion includes one or more support features configured to support the flange within the first housing portion.

31. The portable medical device of clause 30, wherein one of the supports includes a keying feature configured to interact with a keying notch of the flange to orient the flange within the first housing portion.

32. The portable medical device of any one of clauses 29 to 31, wherein the flange includes a lip and an exterior vertical surface from which the lip extends, and wherein the at least a portion of the flange contacting the interior wall of the first housing portion is the lip of the flange.

33. The portable medical device of clause 31 or 32, wherein the trough is formed between the exterior vertical surface of the flange, the lip of the flange and the interior wall of the first housing portion.

34. A method of forming a housing of a medical device, the method including: nesting a flange within a first housing portion, a lip of the flange contacting an interior wall of the first housing portion to form a trough about an interior perimeter of the first housing portion; depositing a bonding agent in the trough, the bonding agent configured to couple the flange to the first housing portion when cured; and coupling a second housing portion to the first housing portion such that an exterior perimeter of the second housing portion is substantially aligned with an exterior perimeter of the first housing portion.

35. The method of clause 34, wherein the bonding agent is deposited by an automated depositor.

36. The method of clause 34 or 35, wherein depositing the bonding agent in the trough includes depositing the bonding agent in multiple passes about the trough.

37. The method of any one of clauses 34 to 36, wherein the second housing portion is releasably coupled to the flange to couple the second housing portion to the first housing portion.

38. The method of any one of clauses 34 to 37, further including aligning a keying feature of the first housing portion with a keying notch of the flange to orient the flange when nested within the first housing portion.

39. A housing for an external defibrillator that is waterproof and shockproof, the housing including: a first portion including an interior wall and a support extending from the interior wall, the first portion of the housing configured to contain an electronic component of the external defibrillator disposed therein; a flange coupled to the first portion of the housing, the flange nested at least partially within the first portion of the housing and supported by the support, wherein the flange and the interior wall form a trench that extends along the interior wall; an adhesive disposed in the trench, the adhesive bonding the flange to the interior wall; and a second portion configured to be coupled to the flange to substantially enclose the electronic component within an interior of the housing when the second portion of the housing is coupled to the flange.

40. The housing of clause 39, wherein: the first portion of the housing is in a shape of a rectangular cuboid; and the flange has a rectangular shape.

41. An external defibrillator including: a housing to contain a component of the external defibrillator, the housing including: a first portion including a closed end, an open end, and an interior wall between the closed end and the open end; a flange coupled to the first portion of the housing, the flange nested at least partially within the first portion of the housing and positioned at the open end, wherein the flange is in contact with the interior wall to form a trench between the flange and the first portion of the housing; an adhesive disposed within the trench, the adhesive bonding the flange to the first portion of the housing; and a second portion configured to be coupled to the flange to substantially enclose the component within an interior of the housing when the second portion of the housing is coupled to the flange.

42. A method of forming a housing of an external defibrillator, the method including: nesting a flange at least partially within a first portion of the housing such that the flange comes into contact with a support extending from an interior wall of the first portion of the housing, and such that a lip of the flange comes into contact with the interior wall to form a trench between the flange and the first portion of the housing, the trench extending along the interior wall; depositing an adhesive in the trench, the adhesive configured to bond the flange to the first portion of the housing when the adhesive is cured; and coupling a second portion of the housing to the flange.

The features disclosed in the foregoing description, or the following claims, or the accompanying drawings, expressed in their specific forms or in terms of a means for performing the disclosed function, or a method or process for attaining the disclosed result, as appropriate, may, separately, or in any combination of such features, be used for realizing the disclosed techniques and systems in diverse forms thereof.

As will be understood by one of ordinary skill in the art, each implementation disclosed herein can comprise, consist essentially of or consist of its particular stated element, step, or component. Thus, the terms "include" or "including" should be interpreted to recite: "comprise, consist of, or consist essentially of." The transition term "comprise" or "comprises" means has, but is not limited to, and allows for the inclusion of unspecified elements, steps, ingredients, or components, even in major amounts. The transitional phrase "consisting of" excludes any element, step, ingredient or component not specified. The transition phrase "consisting essentially of" limits the scope of the implementation to the specified elements, steps, ingredients or components and to those that do not materially affect the implementation. As used herein, the term "based on" is equivalent to "based at least partly on," unless otherwise specified.

Unless otherwise indicated, all numbers expressing quantities used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present disclosure. At the very least, and not as an attempt to limit the application of the doctrine of equivalents to the scope of the claims, each numerical parameter should at least be construed in light of the number of reported significant digits and by applying ordinary rounding techniques. When further clarity is required, the term "about" has the meaning reasonably ascribed to it by a person skilled in the art when used in conjunction with a stated numerical value or range, i.e. denoting somewhat more or somewhat less than the stated value or range, to within a range of ±20% of the stated value; 19% of the stated value; ±18% of the stated value; 17% of the stated value; 16% of the stated value; 15% of the stated value; 14% of the stated value; ±13% of the stated value; ±12% of the stated value; 11% of the stated value; 10% of the stated value; 9% of the stated value; 8% of the stated value; 7% of the stated value; 6% of the stated value; 5% of the stated value; ±4% of the stated value; 3% of the stated value; 2% of the stated value; or ±1% of the stated value.

The invention claimed is:

1. A housing for an external defibrillator that is waterproof and shockproof, the housing comprising:
    a first portion comprising an interior wall and a support extending from the interior wall, the first portion of the housing configured to contain an electronic component of the external defibrillator disposed therein;
    a flange coupled to the first portion of the housing, the flange nested at least partially within the first portion of the housing and supported by the support, wherein the flange and the interior wall form a trench that extends along the interior wall;
    an adhesive disposed in the trench, the adhesive bonding the flange to the interior wall; and
    a second portion configured to be coupled to the flange to substantially enclose the electronic component within an interior of the housing when the second portion of the housing is coupled to the flange.

2. The housing of claim 1, wherein the flange comprises a lip that extends from an exterior surface of the flange, and wherein the trench is formed by the exterior surface of the flange, the lip of the flange, and the interior wall.

3. The housing of claim 2, wherein the support is in contact with a rear side of the lip of the flange to support the flange within the first portion of the housing.

4. The housing of claim 2, wherein the first portion of the housing further comprises a tab extending from the interior wall, and wherein the tab is in contact with a front side of the lip of the flange to retain the flange within the first portion of the housing.

5. The housing of claim 1, wherein the flange comprises openings defined in a front surface of the flange, the openings configured to receive fasteners to couple the second portion of the housing to the flange.

6. The housing of claim 5, wherein the second portion of the housing comprises a bezel configured to cover the fasteners upon coupling the second portion of the housing to the flange.

7. The housing of claim 1, wherein the first portion of the housing comprises a keying feature extending from the interior wall, wherein the flange comprises a keying slot defined in a rear side of the flange, and wherein the keying feature is disposed within the keying slot to orient the flange within the first portion of the housing.

8. The housing of claim 1, wherein:
    the first portion of the housing is in a shape of a rectangular cuboid; and
    the flange has a rectangular shape.

9. An external defibrillator comprising:
    a housing to contain a component of the external defibrillator, the housing comprising:
        a first portion comprising a closed end, an open end, and an interior wall between the closed end and the open end;
        a flange coupled to the first portion of the housing, the flange nested at least partially within the first portion of the housing and positioned at the open end, wherein the flange is in contact with the interior wall to form a trench between the flange and the first portion of the housing;
        an adhesive disposed within the trench, the adhesive bonding the flange to the first portion of the housing; and
        a second portion configured to be coupled to the flange to substantially enclose the component within an interior of the housing when the second portion of the housing is coupled to the flange.

10. The external defibrillator of claim 9, wherein the first portion of the housing further comprises a support extending from the interior wall and supporting the flange within the first portion of the housing.

11. The external defibrillator of claim 10, wherein the flange comprises a lip, and wherein a cutout is defined in the support to receive the lip of the flange.

12. The external defibrillator of claim 9, wherein the first portion of the housing further comprises a keying feature extending from the interior wall and disposed within a keying slot defined in the flange to orient the flange within the first portion of the housing.

13. The external defibrillator of claim 9, wherein the flange comprises a lip and an exterior surface from which the lip extends, and wherein the lip of the flange is in contact with the interior wall.

14. The external defibrillator of claim 13, wherein the first portion of the housing further comprises a tab extending from the interior wall, and wherein the tab is in contact with a front side of the lip of the flange to retain the flange within the first portion of the housing.

15. The external defibrillator of claim 9, wherein the flange comprises openings defined in a front surface of the flange, the openings configured to receive fasteners to couple the second portion of the housing to the flange.

16. The external defibrillator of claim 15, wherein the second portion of the housing comprises a bezel configured to cover the fasteners upon coupling the second portion of the housing to the flange.

17. A method of forming the housing of the external defibrillator of claim 9, the method comprising:
    nesting the flange at least partially within the first portion of the housing such that the flange comes into contact with a support extending from the interior wall of the first portion of the housing, and such that a lip of the flange comes into contact with the interior wall to form the trench between the flange and the first portion of the housing, the trench extending along the interior wall;
    depositing the adhesive in the trench, the adhesive being configured to bond the flange to the first portion of the housing when the adhesive is cured; and
    coupling the second portion of the housing to the flange.

18. The method of claim 17, wherein the depositing comprises depositing the adhesive using an automated depositor.

19. The method of claim 17, wherein the depositing comprises depositing the adhesive in multiple passes along the trench.

20. The method of claim 17, further comprising, prior to the nesting, aligning a keying feature of the first portion of the housing with a keying slot defined in the flange to orient the flange within the first portion of the housing.

* * * * *